United States Patent
Ben Nun

(10) Patent No.: US 11,224,505 B2
(45) Date of Patent: Jan. 18, 2022

(54) HYBRID ACCOMMODATING INTRAOCULAR LENS ASSEMBLAGES INCLUDING DISCRETE LENS UNIT WITH SEGMENTED LENS HAPTICS

(71) Applicant: RAYNER INTRAOCULAR LENSES LIMITED, Worthing (GB)

(72) Inventor: Joshua Ben Nun, Beit-Herut (IL)

(73) Assignee: RAYNER INTRAOCULAR LENSES LIMITED, Worthing West (GB)

( * ) Notice: Subject to any disclaimer, the term of this patent is extended or adjusted under 35 U.S.C. 154(b) by 0 days.

(21) Appl. No.: 17/290,598

(22) PCT Filed: Nov. 4, 2019

(86) PCT No.: PCT/GB2019/053118
§ 371 (c)(1),
(2) Date: Apr. 30, 2021

(87) PCT Pub. No.: WO2020/089657
PCT Pub. Date: May 7, 2020

(65) Prior Publication Data
US 2021/0307898 A1  Oct. 7, 2021

(30) Foreign Application Priority Data

Nov. 2, 2018 (GB) ..................... 1817955

(51) Int. Cl.
*A61F 2/16* (2006.01)
(52) U.S. Cl.
CPC .......... *A61F 2/1648* (2013.01); *A61F 2/1627* (2013.01); *A61F 2002/1689* (2013.01); *A61F 2002/16901* (2015.04)

(58) Field of Classification Search
CPC ................ A61F 2/1648; A61F 2/1627; A61F 2002/16901; A61F 2002/1689
See application file for complete search history.

(56) References Cited

U.S. PATENT DOCUMENTS

| | | |
|---|---|---|
| 3,950,082 A | 4/1976 | Volk |
| 4,122,556 A | 10/1978 | Poler |
| 4,254,509 A | 3/1981 | Tennant |
| 4,298,994 A | 11/1981 | Clayman |
| 4,340,979 A | 7/1982 | Kelman |
| 4,409,690 A | 10/1983 | Gess |
| 4,409,691 A | 10/1983 | Levy |
| 4,445,998 A | 5/1984 | Kanda et al. |

(Continued)

FOREIGN PATENT DOCUMENTS

| | | |
|---|---|---|
| FR | 2794965 A1 | 12/2000 |
| WO | 83/00998 A1 | 3/1983 |

(Continued)

*Primary Examiner* — Leslie Lopez
(74) *Attorney, Agent, or Firm* — Novick, Kim & Lee, PLLC; Harold L. Novick; Hyun Woo Shin

(57) ABSTRACT

Hybrid Accommodating Intra Ocular Lens (AIOL) assemblages including two discrete component parts in the form of a discrete base member for initial implantation in a vacated capsular bag and a discrete lens unit for subsequent implantation in the vacated capsular bag for anchoring to the discrete base member. The lens unit includes a lens optics having at least two segmented lens haptics radially outwardly extending therefrom.

10 Claims, 10 Drawing Sheets

(56) References Cited

U.S. PATENT DOCUMENTS

| | | |
|---|---|---|
| 4,446,581 A | 5/1984 | Blake |
| 4,494,254 A | 1/1985 | Lopez |
| 4,530,117 A | 7/1985 | Kelman |
| RE31,963 E | 8/1985 | Kelman |
| 4,556,998 A | 12/1985 | Siepser |
| 4,575,374 A | 3/1986 | Anis |
| 4,581,033 A | 4/1986 | Callahan |
| 4,589,147 A | 5/1986 | Nevyas |
| 4,591,358 A | 5/1986 | Kelman |
| 4,615,701 A | 10/1986 | Woods |
| 4,671,283 A | 6/1987 | Hoskin |
| 4,676,794 A | 6/1987 | Kelman |
| 4,750,904 A | 6/1988 | Price, Jr. |
| 4,808,181 A | 2/1989 | Kelman |
| 4,842,601 A | 6/1989 | Smith |
| 4,865,601 A | 9/1989 | Caldwell et al. |
| RE33,093 E | 10/1989 | Schiraldi et al. |
| 4,888,012 A | 12/1989 | Horn et al. |
| 4,892,543 A | 1/1990 | Turley |
| 4,932,966 A | 6/1990 | Christie et al. |
| 4,932,968 A | 6/1990 | Caldwell |
| 4,957,505 A | 9/1990 | McDonald |
| 4,969,897 A | 11/1990 | Kalb |
| 4,976,732 A | 12/1990 | Vorosmarthy |
| 4,990,159 A | 2/1991 | Kraff |
| 5,026,373 A | 6/1991 | Ray et al. |
| 5,078,742 A | 1/1992 | Dahan |
| 5,171,268 A | 12/1992 | Ting et al. |
| 5,176,701 A | 1/1993 | Dusek et al. |
| 5,275,623 A | 1/1994 | Sarfarazi |
| 5,282,851 A | 2/1994 | Jacob-LaBarre |
| 5,288,293 A | 2/1994 | O'Donnell, Jr. |
| 5,336,262 A | 8/1994 | Chu |
| 5,346,502 A | 9/1994 | Estabrook et al. |
| 5,476,512 A | 12/1995 | Sarfarazi |
| 5,476,514 A | 12/1995 | Cumming |
| 5,476,515 A | 12/1995 | Kelman et al. |
| 5,484,447 A | 1/1996 | Waldock et al. |
| 5,489,302 A | 2/1996 | Skottun |
| 5,496,366 A | 3/1996 | Cumming |
| 5,522,891 A | 6/1996 | Klaas |
| 5,567,365 A | 10/1996 | Weinschenk, I et al. |
| 5,571,177 A | 11/1996 | Deacon et al. |
| 5,584,304 A | 12/1996 | Brady |
| 5,607,472 A | 3/1997 | Thompson |
| 5,628,795 A | 5/1997 | Langerman |
| 5,674,282 A | 10/1997 | Cumming |
| 5,684,637 A | 11/1997 | Floyd |
| 5,722,952 A | 3/1998 | Schachar |
| 5,752,960 A | 5/1998 | Nallakrishnan |
| 5,843,188 A | 12/1998 | McDonald |
| 5,871,455 A | 2/1999 | Ueno |
| 5,895,610 A | 4/1999 | Chang et al. |
| 5,919,230 A | 7/1999 | Sambursky |
| 5,968,094 A | 10/1999 | Werblin et al. |
| 5,984,962 A | 11/1999 | Anello et al. |
| 6,007,579 A | 12/1999 | Lipshitz et al. |
| 6,013,101 A * | 1/2000 | Israel ............ A61F 2/1648 623/6.43 |
| 6,027,531 A | 2/2000 | Tassignon |
| 6,051,024 A | 4/2000 | Cumming |
| 6,110,202 A | 8/2000 | Barraquer et al. |
| 6,117,171 A | 9/2000 | Skottun |
| 6,129,759 A | 10/2000 | Chambers |
| 6,129,760 A | 10/2000 | Fedoraov et al. |
| 6,164,282 A | 12/2000 | Gwon et al. |
| 6,176,878 B1 | 1/2001 | Gwon et al. |
| 6,193,750 B1 | 2/2001 | Cumming |
| 6,197,057 B1 | 3/2001 | Peyman et al. |
| 6,197,059 B1 | 3/2001 | Cumming |
| 6,200,342 B1 | 3/2001 | Tassignon |
| 6,280,469 B1 | 8/2001 | Terry et al. |
| 6,280,471 B1 | 8/2001 | Peyman |
| 6,299,618 B1 | 10/2001 | Sugiura |
| 6,299,641 B1 | 10/2001 | Woods |
| 6,342,073 B1 | 1/2002 | Cumming et al. |
| 6,387,126 B1 | 5/2002 | Cumming |
| 6,406,494 B1 | 6/2002 | Laguette |
| 6,423,094 B1 | 7/2002 | Sarfarazi |
| 6,443,984 B1 | 9/2002 | Jahn et al. |
| 6,443,985 B1 | 9/2002 | Woods |
| 6,464,725 B2 | 10/2002 | Skottun |
| 6,488,708 B2 | 12/2002 | Sarfarazi |
| 6,494,910 B1 | 12/2002 | Ganem et al. |
| 6,494,911 B2 | 12/2002 | Cumming |
| 6,503,276 B2 | 1/2003 | Lang et al. |
| 6,506,212 B2 | 1/2003 | Zhou |
| 6,520,691 B2 | 2/2003 | Nomura |
| 6,524,340 B2 | 2/2003 | Israel |
| 6,554,860 B2 | 4/2003 | Hoffmann et al. |
| 6,570,718 B2 | 5/2003 | Nomura |
| 6,596,026 B1 | 7/2003 | Gross et al. |
| 6,599,317 B1 | 7/2003 | Joseph, III et al. |
| 6,605,093 B1 | 8/2003 | Blake |
| 6,616,692 B1 | 9/2003 | Glick et al. |
| 6,638,305 B2 | 10/2003 | Laguette |
| 6,638,306 B2 | 10/2003 | Cumming |
| 6,645,245 B1 | 11/2003 | Preussner |
| 6,739,722 B2 | 5/2004 | Laguette |
| 6,749,634 B2 | 6/2004 | Hanna |
| 6,827,738 B2 | 12/2004 | Willis et al. |
| 6,849,091 B1 | 2/2005 | Cumming |
| 6,960,231 B2 | 11/2005 | Tran |
| 6,970,232 B2 | 11/2005 | Mcguire, Jr. |
| 6,972,033 B2 | 12/2005 | McNicholas |
| 7,008,449 B2 | 3/2006 | Willis et al. |
| 7,025,783 B2 | 4/2006 | Brady |
| 7,037,338 B2 | 5/2006 | Nagamoto |
| 7,097,660 B2 | 8/2006 | Portney |
| 7,118,597 B2 | 10/2006 | Miller et al. |
| 7,122,053 B2 | 10/2006 | Esch |
| 7,137,994 B2 | 11/2006 | Juan, Jr. et al. |
| 7,220,279 B2 | 5/2007 | Nun |
| 7,261,737 B2 | 8/2007 | Esch et al. |
| 7,278,739 B2 | 10/2007 | Shadduck |
| 7,350,916 B2 | 4/2008 | Hong |
| 7,815,678 B2 | 10/2010 | Ben Nun |
| 7,842,087 B2 | 11/2010 | Ben Nun |
| 7,854,764 B2 | 12/2010 | Ben Nun |
| 7,857,850 B2 | 12/2010 | Mentak et al. |
| 7,976,520 B2 | 7/2011 | Nun |
| 7,981,155 B2 | 7/2011 | Cumming |
| 7,998,199 B2 | 8/2011 | Ben Nun |
| 8,034,106 B2 | 10/2011 | Mentak |
| 8,048,155 B2 | 11/2011 | Shadduck |
| 8,048,156 B2 | 11/2011 | Geraghty et al. |
| 8,057,217 B2 | 11/2011 | Graney et al. |
| 8,088,161 B2 | 1/2012 | Aharoni et al. |
| 8,273,123 B2 | 9/2012 | Ben Nun |
| 8,382,831 B2 | 2/2013 | Ben Nun |
| 8,398,709 B2 | 3/2013 | Ben Nun |
| 8,734,509 B2 | 5/2014 | Mentak et al. |
| 8,801,781 B2 | 8/2014 | Tabernero |
| 8,834,565 B2 | 9/2014 | Ben Nun |
| 9,814,568 B2 | 11/2017 | Ben Nun |
| 2002/0103535 A1 | 8/2002 | Portney |
| 2002/0138140 A1* | 9/2002 | Hanna ............ A61F 2/1629 623/6.37 |
| 2003/0060881 A1 | 3/2003 | Glick et al. |
| 2003/0097177 A1 | 5/2003 | Tran |
| 2003/0204254 A1 | 10/2003 | Pen Qun et al. |
| 2003/0204256 A1* | 10/2003 | Peng ............ A61F 2/1629 623/6.34 |
| 2004/0073304 A1 | 4/2004 | Weinschenk |
| 2004/0148022 A1 | 7/2004 | Eggleston |
| 2005/0107875 A1 | 5/2005 | Cumming |
| 2005/0177229 A1 | 8/2005 | Boxer Wachler |
| 2006/0069433 A1 | 3/2006 | Nun |
| 2006/0074487 A1 | 4/2006 | Gilg |
| 2007/0027541 A1 | 2/2007 | Aharoni et al. |
| 2007/0088433 A1 | 4/2007 | Esch et al. |
| 2007/0123981 A1 | 5/2007 | Tassignon |
| 2007/0129799 A1 | 6/2007 | Schedler |
| 2007/0129803 A1 | 6/2007 | Cumming et al. |

(56) References Cited

U.S. PATENT DOCUMENTS

| | | |
|---|---|---|
| 2007/0260308 A1 | 11/2007 | Tran |
| 2007/0260309 A1 | 11/2007 | Richardson |
| 2008/0086208 A1 | 4/2008 | Nordan |
| 2008/0154362 A1* | 6/2008 | Cumming ................ A61F 2/16 623/6.37 |
| 2008/0161914 A1 | 7/2008 | Brandy et al. |
| 2009/0198247 A1 | 8/2009 | Ben Nun |
| 2010/0016965 A1 | 1/2010 | Hong et al. |
| 2011/0313519 A1 | 12/2011 | Cumming |
| 2013/0116781 A1 | 5/2013 | Ben Nun |
| 2013/0304206 A1 | 11/2013 | Pallikaris et al. |
| 2014/0309734 A1 | 10/2014 | Sohn et al. |

FOREIGN PATENT DOCUMENTS

| | | |
|---|---|---|
| WO | 98/05273 A1 | 2/1998 |
| WO | 98/10717 A1 | 3/1998 |
| WO | 99/29266 A1 | 6/1999 |
| WO | 99/62434 A1 | 12/1999 |
| WO | 00/30566 A1 | 6/2000 |
| WO | 01/08606 A1 | 2/2001 |
| WO | 03/105669 A2 | 12/2003 |
| WO | 2008/112879 A2 | 9/2008 |
| WO | 2009/122409 A1 | 10/2009 |
| WO | 2016/191614 A1 | 12/2016 |
| WO | 2017/203517 A1 | 11/2017 |

* cited by examiner

HYBRID ACCOMMODATING INTRAOCULAR LENS ASSEMBLAGES INCLUDING DISCRETE LENS UNIT WITH SEGMENTED LENS HAPTICS

FIELD OF THE INVENTION

This invention relates to accommodating intraocular lens assemblages in general and in-the-bag accommodating intraocular lens assemblages in particular.

BACKGROUND OF THE INVENTION

Referring to FIG. 1 and FIG. 2, the structure and operation of a human eye are described as context for the present invention. FIG. 1 and FIG. 2 are cross section views of an anterior part of a human eye 10 having a visual axis VA for near vision and distance vision, respectively, in an axial plane of the human body. The human eye 10 has an anterior transparent cap like structure known as a cornea 11 connected at its circumferential periphery to a spherical exterior body made of tough connective tissue known as sclera 12 at an annular corneal limbus 13. An iris 14 inwardly extends into the human eye 10 from its root 16 at the corneal limbus 13 to divide the human eye's anterior part into an anterior chamber 17 and a posterior chamber 18. The iris 14 is a thin annular muscle structure with a central pupil. The iris 14 is activated by inter alia ambient light conditions, focusing for near vision, and other factors for a consequential change in pupil diameter. An annular ciliary body 19 is connected to zonular fibers 21 which in turn are peripherally connected to an equatorial edge of a capsular bag 22 having an anterior capsule 23 and a posterior capsule 24 and containing a natural crystalline lens 26.

Contraction of the ciliary body 19 allows the lens 26 to thicken to its natural thickness T1 along the visual axis VA for greater positive optical power for near vision (see FIG. 1). Relaxation of the ciliary body 19 tensions the zonular fibers 21 which circumferentially draws the capsular bag 22 radially outward as shown by arrows A for compressing the lens 26 to shorten its thickness along the visual axis VA to T2<T1 for lower positive optical power for distance vision (see FIG. 2). Cataract surgery involves capsulorrhexis in an anterior capsule 23 for enabling removal of a natural crystalline lens 26. Capsulorrhexis typically involves preparing an about 5 mm diameter circular aperture in an anterior capsule 23 to leave an annular anterior capsule flange 27 and an intact posterior capsule 24. FIG. 1 and FIG. 2 denote the boundary of the circular aperture by arrows B.

Near vision is defined at a distance range of between about 33 cm to 40 cm and requires an additional positive optical power of between about 2.5 Diopter to 23 Diopter over best corrected distance vision. Healthy human eyes undergo pupillary miosis to about 2 mm pupil diameter for near vision from an about 3 mm to 6 mm pupil diameter for distance vision corresponding to ambient illumination conditions. Ciliary body relaxation in healthy human eyes is capable of application of a patient specific accommodative physiological force on a natural crystalline lens. Maximal accommodative physiological forces occur for distance vision with the ciliary muscles relaxed and the capsular bag circumferentially stretched by the zonuli connecting the ciliary body to the lens capsule. Maximal accommodative physiological forces are estimated to be in the 10 gram force range depending on a patient's age, eye size, and other factors. Minimal near zero gram force accommodative physiological forces occur for near vision with the zonuli being untaut.

Commonly owned PCT International Application No. PCT/IL2017/050566 entitled Hybrid Accommodating Intraocular Lens Assemblages published under PCT International Publication No. WO 2017/203517 A1 discloses hybrid accommodating intraocular lens (AIOL) assemblages having two discrete component parts in the form of a discrete base member for initial implantation in a vacated capsular bag and a discrete lens unit for subsequent implantation in the vacated capsular bag for anchoring thereonto. The WO 2017/203517 hybrid accommodating intraocular lens (AIOL) assemblages are intended to be manufactured from presently commercially available bio-compatible foldable plastic materials known in the IOL industry. The discrete base member has a base member axis and includes a flat circular base member centerpiece and an elevated circumferential retainer bounding a circumferential groove. The discrete lens unit has a lens optics axis intended to be co-axial with the base member axis on mounting the discrete lens unit on the discrete base member. The discrete lens unit includes a lens optics having two diametrical pairs of identical shape memory resiliently flexible lens haptics radially outwardly extending therefrom for anchoring in the circumferential groove.

WO 2017/203517 FIG. 8 shows that in an in-the-hand assembled hybrid AIOL assemblage, the two diametrical pairs of lens haptics are sufficiently stiff to hold the lens optics away from the discrete base member in their unflexed state. In a relaxed ciliary body state for distance vision, the circumferentially stretched vacated capsular bag flexes the lens haptics substantially along their entire lengths for urging the lens optics along the lens optics axis towards the discrete base member such that the posterior lens optics surface is intimately immerged in the anterior base member centerpiece surface to create a single refractive index optical continuum. Accordingly, the lens haptics necessarily have a total compliance less than a patient's maximal accommodative physiological force for distance vision. Conversely, on contraction of the ciliary body for near vision, the capsular bag relaxes and the lens haptics unflex from their WO 2017/203517 FIG. 12 flexed state to their WO 2017/203517 FIG. 11 unflexed state thereby restoring separation between the lens optics and the discrete base member. Thus, the lens haptics are necessarily required to demonstrate considerable shape memory capability for repeated cyclic flexing and unflexing between a relaxed ciliary body state and a contracted ciliary body state. However, it has now been found the lens haptics recovery time is slower than a human's natural response time between near vision and distance vision. Such a lens haptics recovery time leads to undesirable unnatural visual phenomena, for example, a slower than natural focusing on an object.

There is a need for discrete lens units with lens haptics manufactured from presently commercially available bio-compatible shape memory foldable plastic materials suitable for IOL haptics for use in WO 2017/203517 hybrid AIOL assemblages for restoring visual accommodation comparable to natural accommodation of a healthy young human adult eye in terms of accommodation range and response time.

SUMMARY OF THE INVENTION

The present invention is directed towards improved WO 2017/203517 hybrid AIOL assemblages including a discrete lens unit with segmented lens haptics designed for restoring vision accommodation comparable to natural accommodation of healthy young human adult eye in terms of accommodation range and response time. Discrete lens units can include an even or odd number of segmented lens haptics. Each segmented lens haptics includes two or more lens haptics segments between its lens haptics affixed end and its lens haptics free end to enable compliance within the range of a human eye's accommodative physiological force. Accordingly, a segmented lens haptics is designed to flex at a flexible lens haptics segment and not flex at in inflexible lens haptics segment on application of an accommodative physiological force in contradistinction to aforesaid WO 2017/203517 lens haptics intended flexing therealong from its lens haptics affixed end to its lens haptics free end. Such flexibility is afforded by a relatively deep radial groove in a posterior lens haptics surface for reducing the thickness of a part of a lens haptics so that it becomes flexible under a physiologically available force compared to an adjacent part which remains thick and hence inflexible under the same physiologically available force.

Most importantly, a discrete lens unit is designed such that on application of a predetermined compression force, whereupon its posterior lens optics surface is intimately immerged in an anterior base member centerpiece surface, each flexible lens haptics segment of each and every segmented lens haptics is flexed to its maximal degree to close its groove such that a posterior lens haptics surface becomes a single continuous arcuate shape in a transverse cross section of a discrete lens unit co-directional with its discrete lens unit axis as opposed to a staggered arcuate shape without application of a compression force. By virtue of closing of the grooves along its posterior lens haptics surface, each segmented lens haptics becomes a rigid arched structure whereupon the discrete lens unit as a whole becomes a rigid structure which is no longer affected by an additional applied force which inherently occurs during capsular fibrosis and contraction, thereby avoiding tilting or dislocation of a discrete lens unit with consequential optical aberrations.

While maintaining accurate design symmetry for all its two or more segmented lens haptics, compliance of a discrete lens unit can be adjusted by fine tuning one or more design parameters of its segmented lens haptics as follows: First, creating a pivot point along a segmented lens haptics by forming one or more opposite pairs of cutouts between its lens haptics affixed end to its lens haptics free end such that a segmented lens haptics has a smaller arc length between a pair of cutouts compared to its arc length at its lens haptics affixed end and its arc length at its lens haptics free end in a top plan view of its anterior lens optics surface. And second, in the case that a segmented lens haptics includes two or more spaced apart flexible lens haptics segments, the flexible lens haptics segments can be made with different flexibilities such that one flexible lens haptics segment starts to flex before an adjacent flexible lens haptics segment at a lower force within the accommodative physiological force range.

Discrete lens units are preferably formed with a lens optics surround surrounding a lens optics such its two or more spaced apart shape memory resiliently flexible segmented lens haptics radially extend from the lens optics surround. Each segmented lens haptics preferably has a haptics manipulation aperture adjacent thereto in the lens optics surround thereby affording convenient access thereto for dialing purposes of a discrete lens unit to its correct position in an implanted eye.

BRIEF DESCRIPTION OF DRAWINGS

In order to understand the invention and to see how it can be carried out in practice, preferred embodiments will now be described, by way of non-limiting examples only, with reference to the accompanying drawings in which similar parts are likewise numbered, and in which.

DETAILED DESCRIPTION OF DRAWINGS

WO 2017/203517 Hybrid AIOL Assemblages

Figure 1:
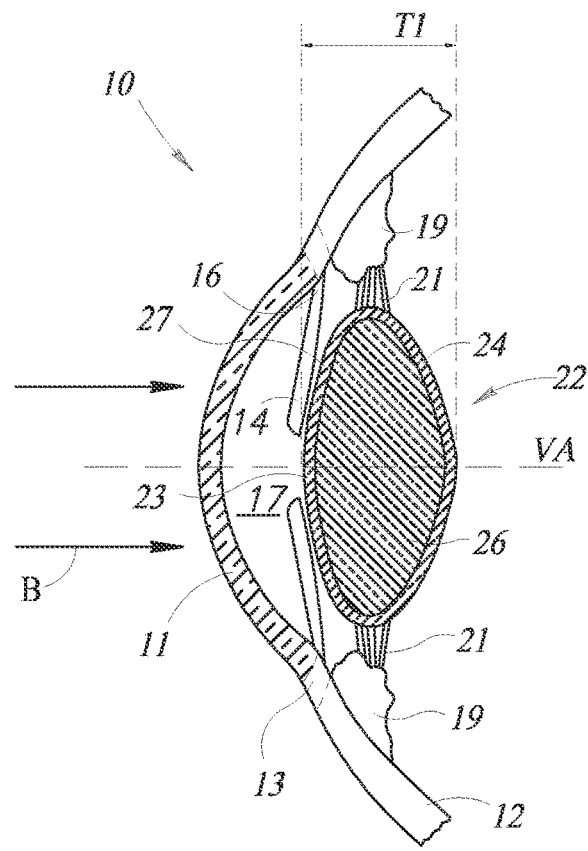
FIG. 1 is a cross section of an anterior part of a human eye in its natural near vision condition in an axial plane of the human body.
Figure 2:
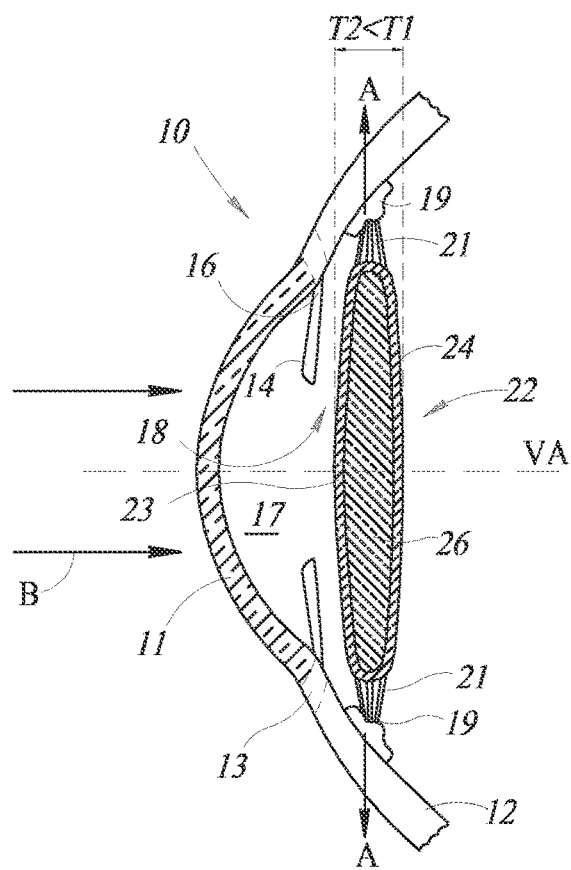
FIG. 2 is a cross section of an anterior part of a human eye in its natural distance vision condition in an axial plane of the human body.
Figure 3:
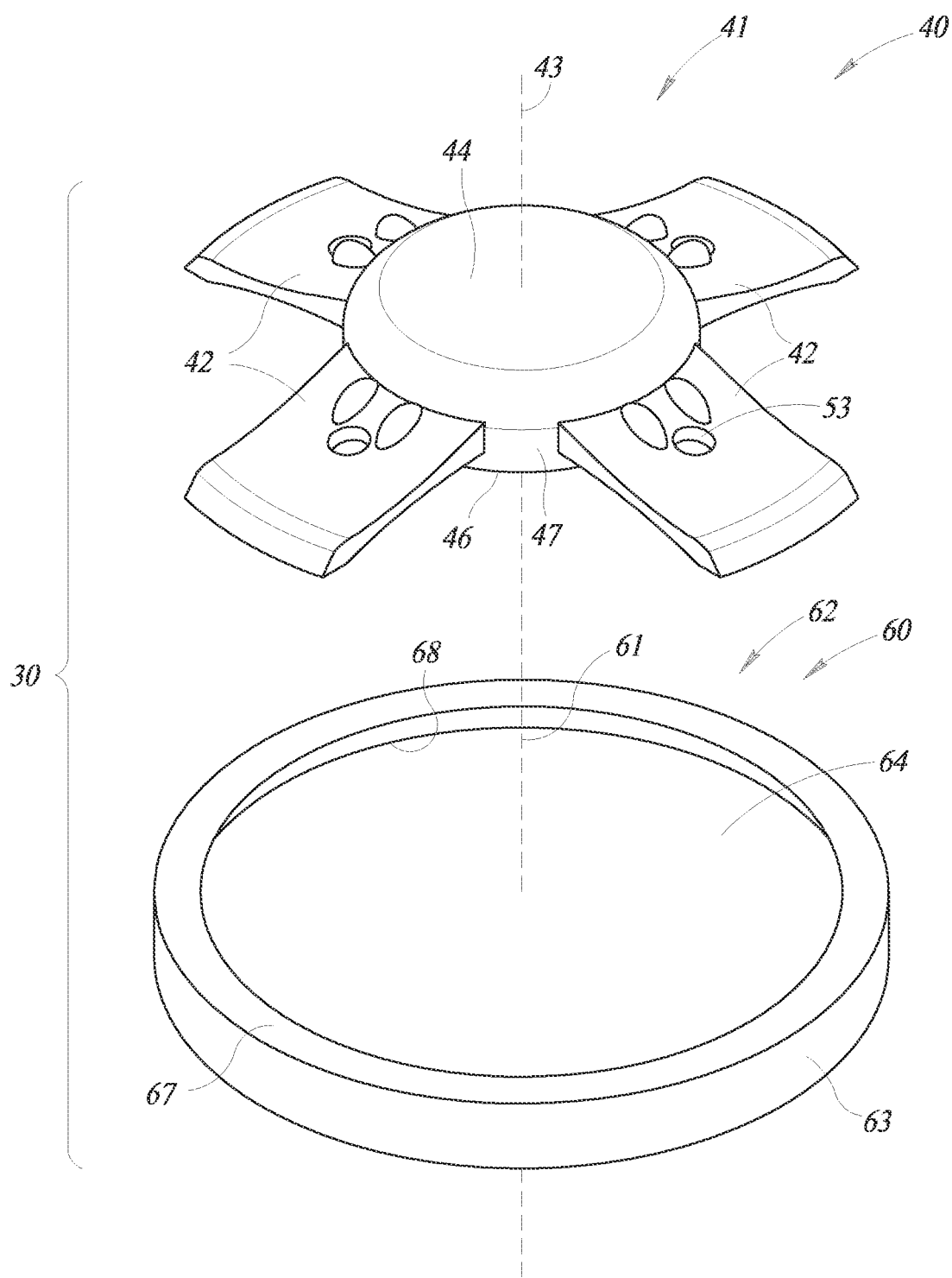
FIG. 3 is a perspective front view of a WO 2017/203517 hybrid AIOL assemblage before assembly corresponding to WO 2017/203517 FIG. 3.
Figure 4:
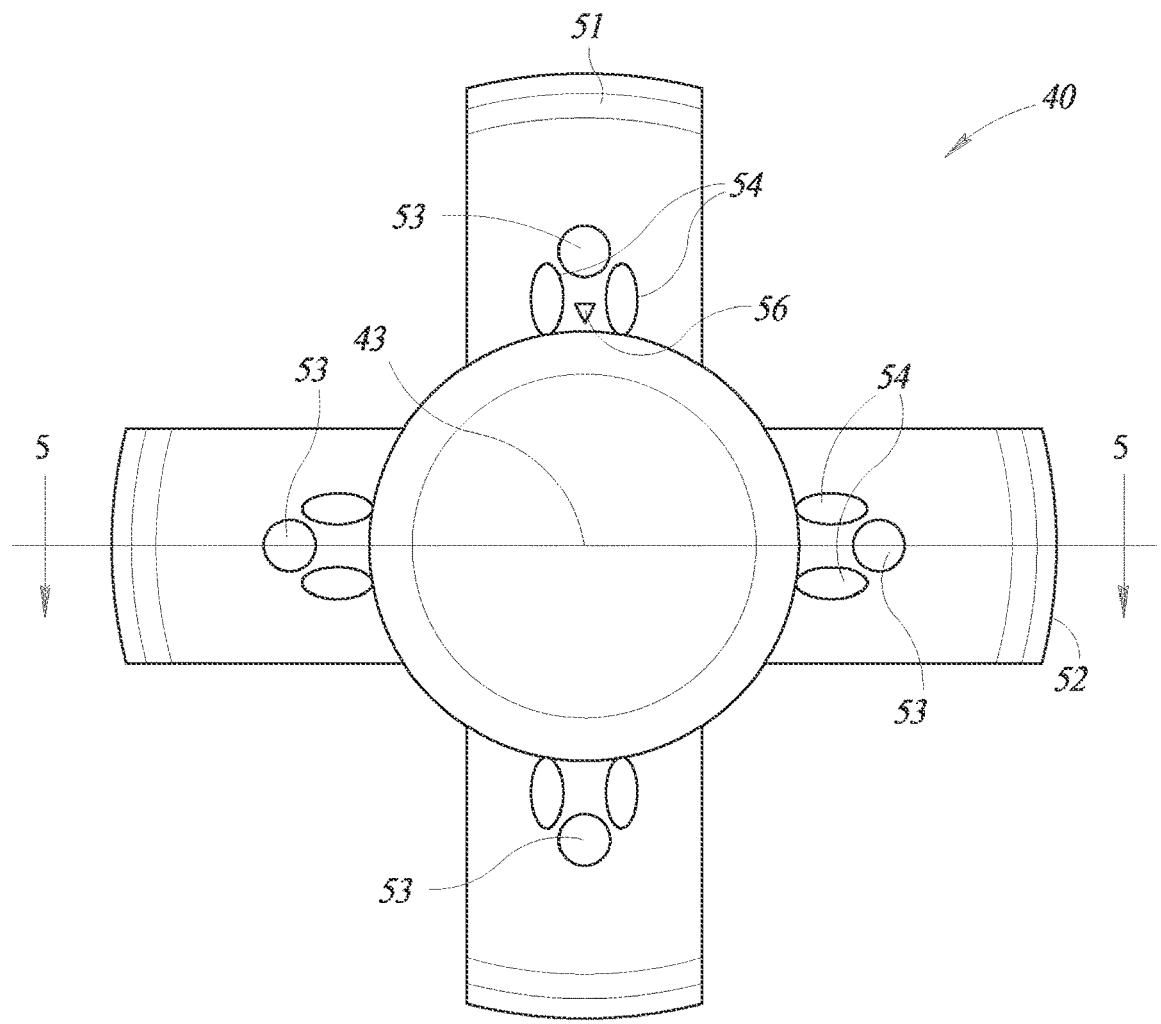
FIG. 4 is a top plan view of a discrete lens unit of the WO 2017/203517 hybrid AIOL assemblage corresponding to WO 2017/203517 FIG. 4.
Figure 5:
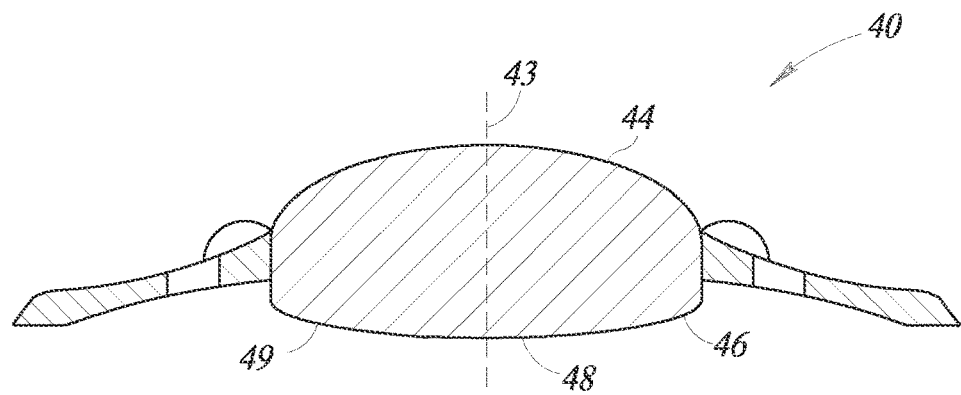
FIG. 5 is a transverse cross section of the WO 2017/203517 discrete lens unit along line 5-5 in FIG. 4 co-directional with a lens optics axis of the discrete lens unit corresponding to WO 2017/203517 FIG. 5.

FIG. 3 to FIG. 5 show a hybrid AIOL assemblage 30 including a discrete lens unit 40 and a discrete base member 60 for in situ assembly in a capsular bag during cataract surgery. The hybrid AIOL assemblage 30 is entirely made from implantable presently commercially available biocompatible material suitable for intraocular lenses.

The discrete lens unit 40 includes a lens optics 41 and two diametric pairs of equispaced shape memory resiliently flexible lens haptics 42 radially outward extending from the lens optics 41. The lens unit 40 can be manufactured as a monolithic structure. Alternatively, the lens haptics 42 can be manufactured separately from the lens optics 41 and attached thereto using industry known attachment technologies. The lens optics 41 has a lens optics axis 43 for co-axial alignment with a human visual axis VA, an anterior lens optics surface 44, a posterior lens optics surface 46 and a lens optics edge 47. The posterior lens optics surface 46 includes a central circle 48 having an approximate 2.5 mm diameter around the lens optics axis 43 corresponding to near vision pupil size under normal reading illumination conditions and a surrounding annular multi-focal segment 49.

The lens haptics 42 has a lens haptics free end 51 with a lens haptics curved edge corresponding to a curvature of an anchoring interface of the discrete base member 60. Each lens haptics 52 preferably has a manipulation aperture 53 and an elongated anterior spacer pair 54 adjacent to the lens optics 41. The discrete lens unit 40 preferably has an optical axis marker 56 for assisting correct alignment with respect to a human visual axis VA on implantation.

The discrete base member 60 has a base member axis 61 and includes a flat circular base member centerpiece 62 and a base member surround 63. The base member 60 can be manufactured as a monolithic structure. Alternatively, the base member surround 63 can be manufactured separately from the base member centerpiece 62 and attached thereto using industry known attachment technologies. The base member centerpiece 62 has a flat circular anterior base member centerpiece surface 64 and a flat circular posterior base member centerpiece surface 66. The base member surround 63 is formed with an elevated circumferential retainer 67 for forming a circumferential groove 68 with the anterior base member centerpiece surface 64 for receiving the lens haptics free ends 51 for anchoring the discrete lens unit 40 on the discrete base member 60.

Figure 6:
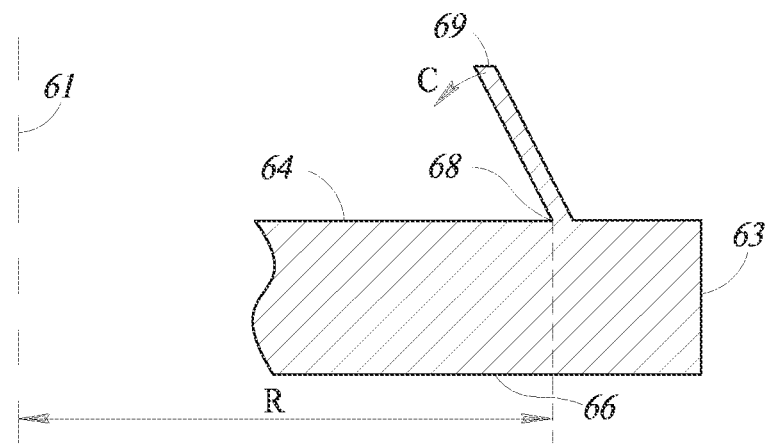
FIG. 6 is a transverse cross section of another discrete base member co-directional with a base member axis of the discrete base member corresponding to WO 2017/203517 FIG. 10.

FIG. 6 shows an alternative elevated circumferential retainer 67 in the form of a pliable rim 69 designed to be flexed towards the anterior base member centerpiece surface 64 by the anterior capsule flange 27 as denoted by arrow C.

Figure 7:
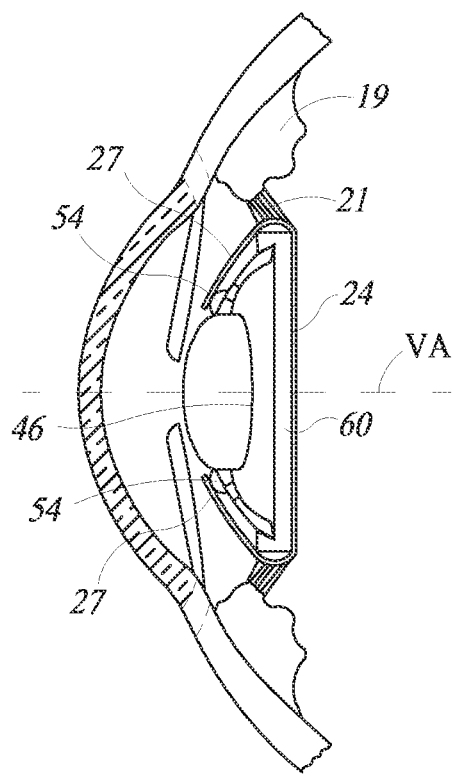
FIG. 7 is a cross section of an implanted WO 2017/203517 hybrid AIOL assemblage for near vision corresponding to WO 2017/203517 FIG. 11.
Figure 8:
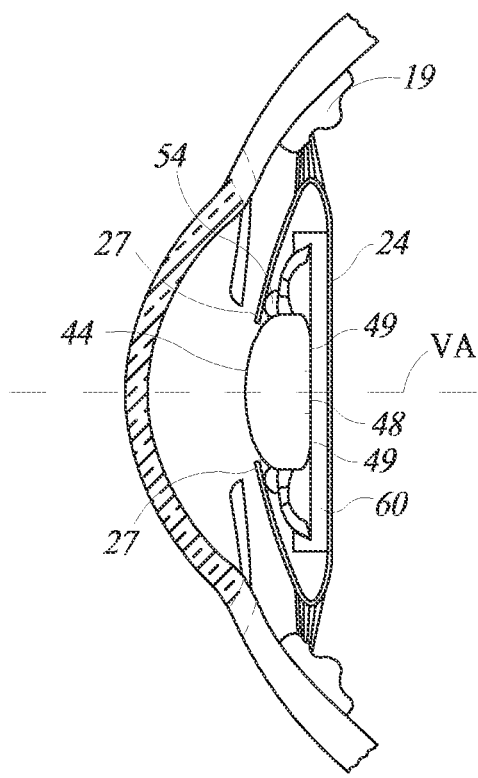
FIG. 8 is a cross section of an implanted WO 2017/203517 hybrid AIOL assemblage for distance vision corresponding to WO 2017/203517 FIG. 12.

FIG. 7 and FIG. 8 are cross sections of an implanted WO 2017/203517 hybrid AIOL assemblage correspondingly for near vision and distance vision.

WO 2017/203517 Hybrid AIOL assemblages with Segmented Lens Haptics

Figure 9:
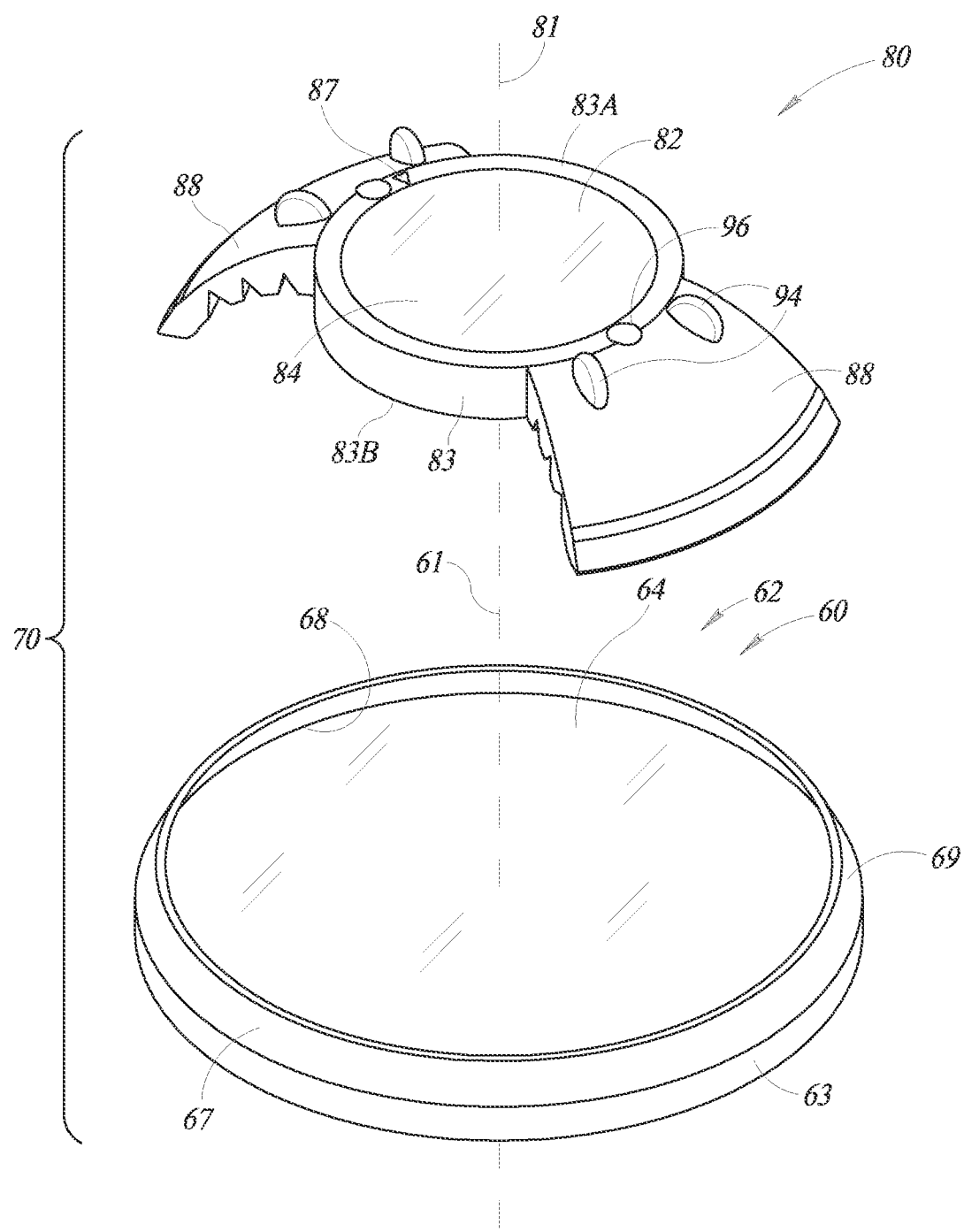
FIG. 9 is a front perspective view of a modified WO 2017/203517 hybrid AIOL assemblage before assembly.
Figure 10:
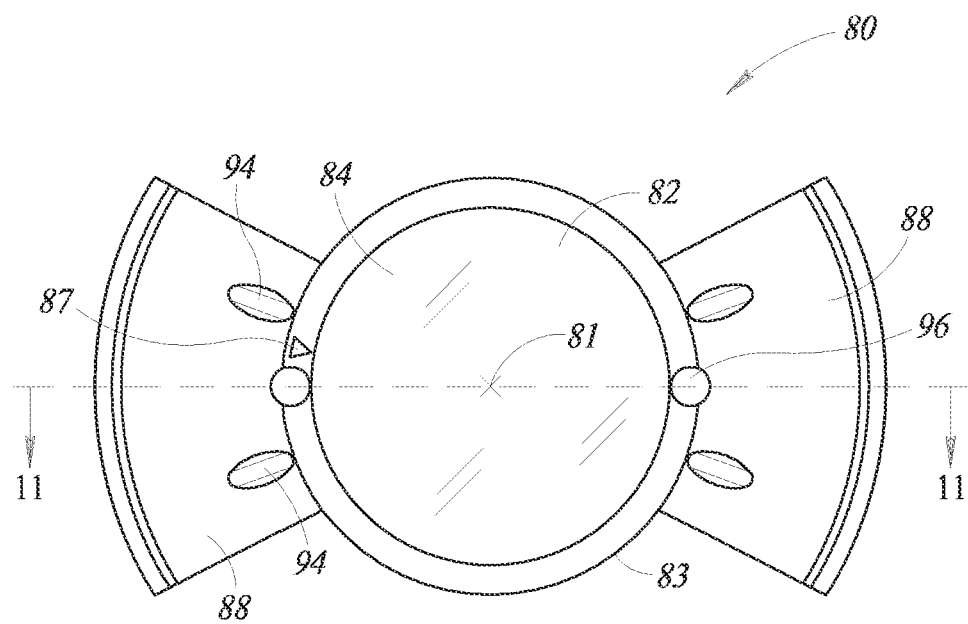
FIG. 10 is a top plan view of the FIG. 9 discrete lens unit.
Figure 11:
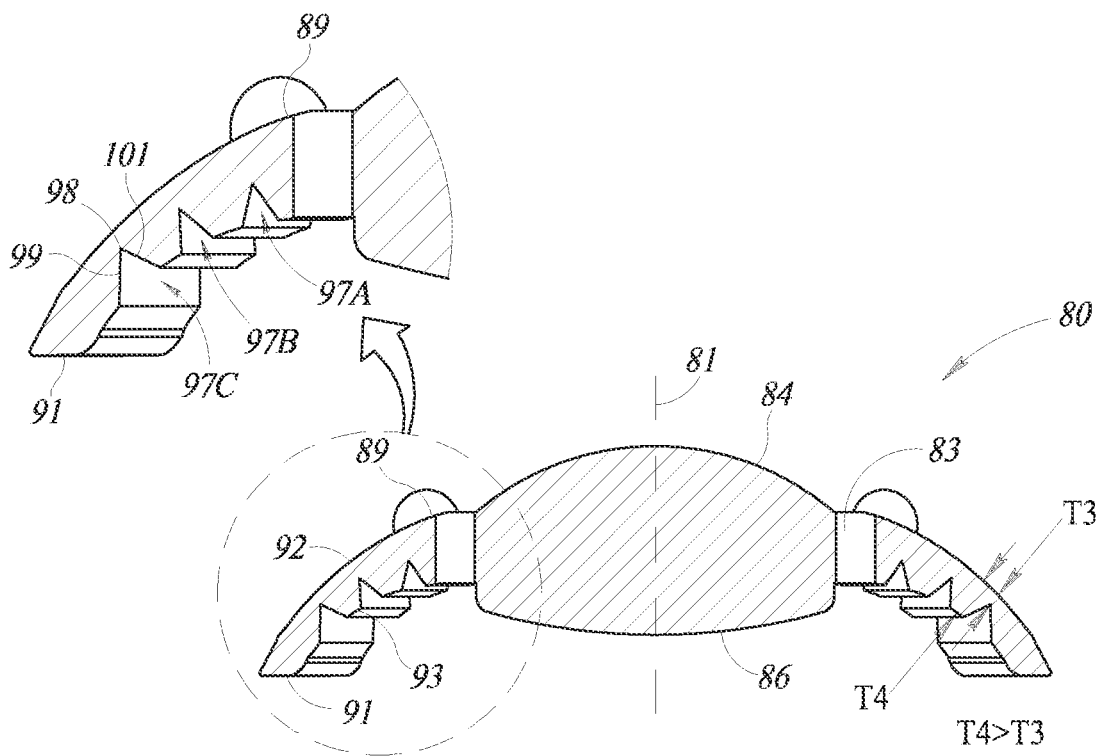
FIG. 11 is a transverse cross section of the FIG. 9 discrete lens unit co-directional with a discrete lens unit axis of the discrete lens unit along line 11-11 in FIG. 10 and an encircled section shown enlarged.

FIG. 9 to FIG. 11 show a hybrid AIOL assemblage 70 having a similar construction and operation as the hybrid AIOL assemblage 30. The hybrid AIOL assemblage 70 includes a discrete lens unit 80 and a discrete base member 60 for in situ assembly in a capsular bag during cataract surgery. The discrete base member 60 is formed with a pliable rim 69 as hereinabove described with reference to FIG. 6 corresponding to WO 2017/203517 FIG. 10.

The discrete lens unit 80 has a discrete lens unit axis 81 and includes a central lens optics 82 and a lens optics surround 83 surrounding the lens optics 82. The lens optics 82 has an anterior lens optics surface 84 similar to the anterior lens optics surface 44 and a posterior lens optics surface 86 similar to the posterior lens optics surface 46. The lens optics 82 has an at least minimum diameter in accordance with prevailing ISO standard requirements. The lens optics surround 83 has an external diameter of between about 6 mm to 7 mm. The lens optics surround 83 has a flat anterior surface 83A and a flat posterior surface 83B both perpendicular to the discrete lens unit axis 81 and therefore with zero optical power. In the case that the lens optics 82 has a toric optical power, the lens optics surround 83 preferably includes an optical axis marker 87 for assisting angular alignment of the discrete lens unit 80 to the required angle with respect to a human visual axis VA during implantation.

The discrete lens unit 80 has a diametric pair of shape memory resiliently flexible segmented lens haptics 88 radially extending from the lens optics surround 83. The segmented lens haptics 88 are made from clinically approved, bio-compatible, implantable shape memory foldable material suitable for lens haptics. The segmented lens haptics 88 are preferably symmetrical and have identical compliance to an applied capsular force such that the entire discrete lens unit 80 reciprocates relative to the discrete base member 60 without tilting with consequential optic aberrations.

Each segmented lens haptics 88 has a monolithic structure in the sense it is manufactured as a single unitary piece from the same material along its entire length from a lens haptics affixed end 89 at the lens optics surround 83 to its lens haptics free end 91. Each segmented lens haptics 88 has an anterior lens haptics surface 92 in the direction of the anterior lens optics surface 84 and a posterior lens haptics surface 93 in the direction of the posterior lens optics surface 86. Each segmented lens haptics 88 includes an elongated anterior spacer pair 94 adjacent to the lens optics surround 83 for spacing an anterior capsule flange 27 from the discrete lens unit's anterior surface for enabling unhindered fluid flow in and out of a capsular bag. Each segmented lens haptics 88 includes a throughgoing haptics manipulation aperture 96 mostly in the lens optics surround 83 for dialing the discrete lens unit 80 around the discrete lens unit axis 81 for setting at a required position.

Each segmented lens haptics 88 has localized flexible segments formed by generally circumferential grooves 97 in the posterior lens haptics surface 93 with respect to the discrete lens unit axis 81. The grooves 97 are generally isosceles triangular shaped in a transverse cross section co-directional with the discrete lens unit axis 81. Each groove 97 includes an apex 98 towards the anterior lens haptics surface 92, a first opposing surface 99 towards the lens haptics affixed end 89 and a second opposing surface 101 towards the lens haptics free end 91 and facing the first opposing surface 99.

Each grooved section of a segmented lens haptics 88 constitutes a flexible lens haptics segment 102 within the range of a human eye's accommodative physiological force. Conversely, each non-grooved section of a segmented lens haptics 88 constitutes an inflexible lens haptics segment 103 within the range of a human eye's accommodative physiological force. A flexible lens haptics segment 102 has a thickness T3 at its apex 98 and an inflexible lens haptics segment 103 has a thickness T4 where T4 >T3. FIG. 11 shows each segmented lens haptics 88 has a staggered arrangement of three grooves 97A, 97B and 97C resulting in three flexible lens haptics segments 102A, 102B and 102C and four inflexible lens haptics segments 103A, 103B, 103C and 103D (see FIG. 12).

Figure 12:
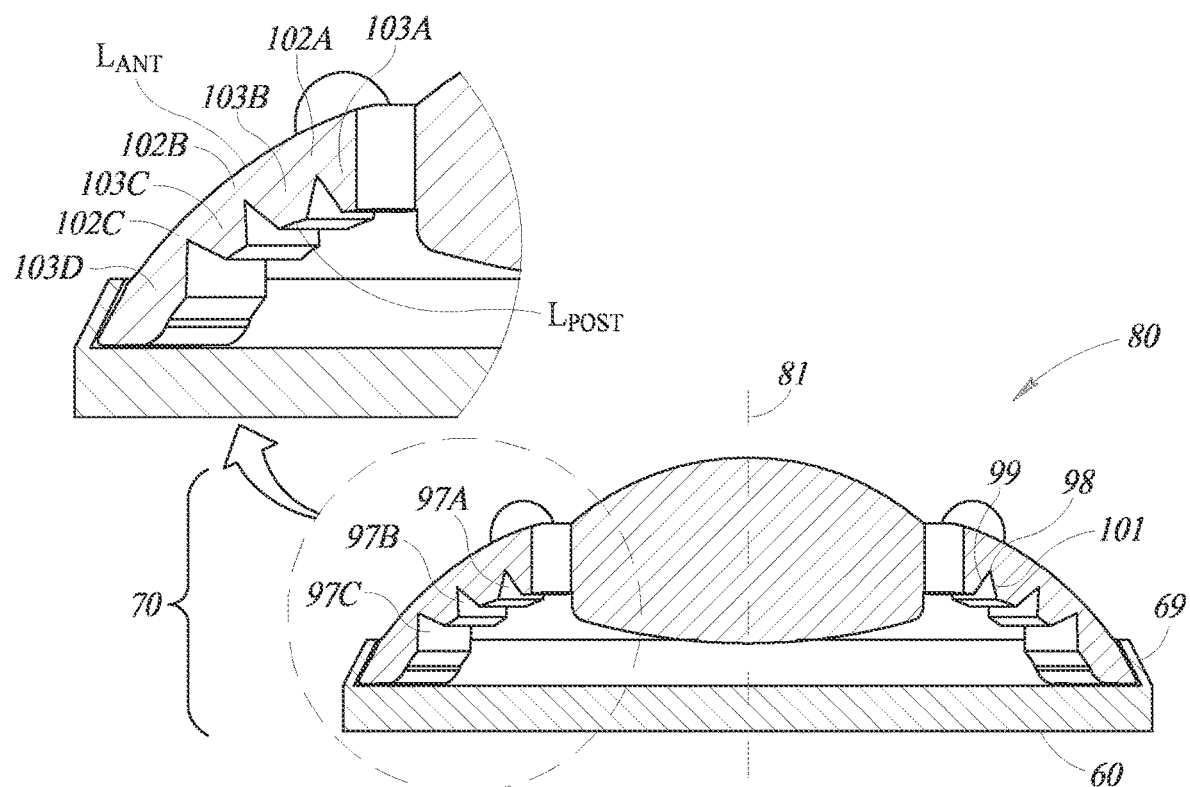
FIG. 12 is a transverse cross section of an assembled hybrid AIOL assemblage including the FIG. 9 discrete lens unit co-directional with the discrete lens unit axis along line 11-11 in FIG. 10 without application of a compression force and an encircled section shown enlarged.
Figure 13:
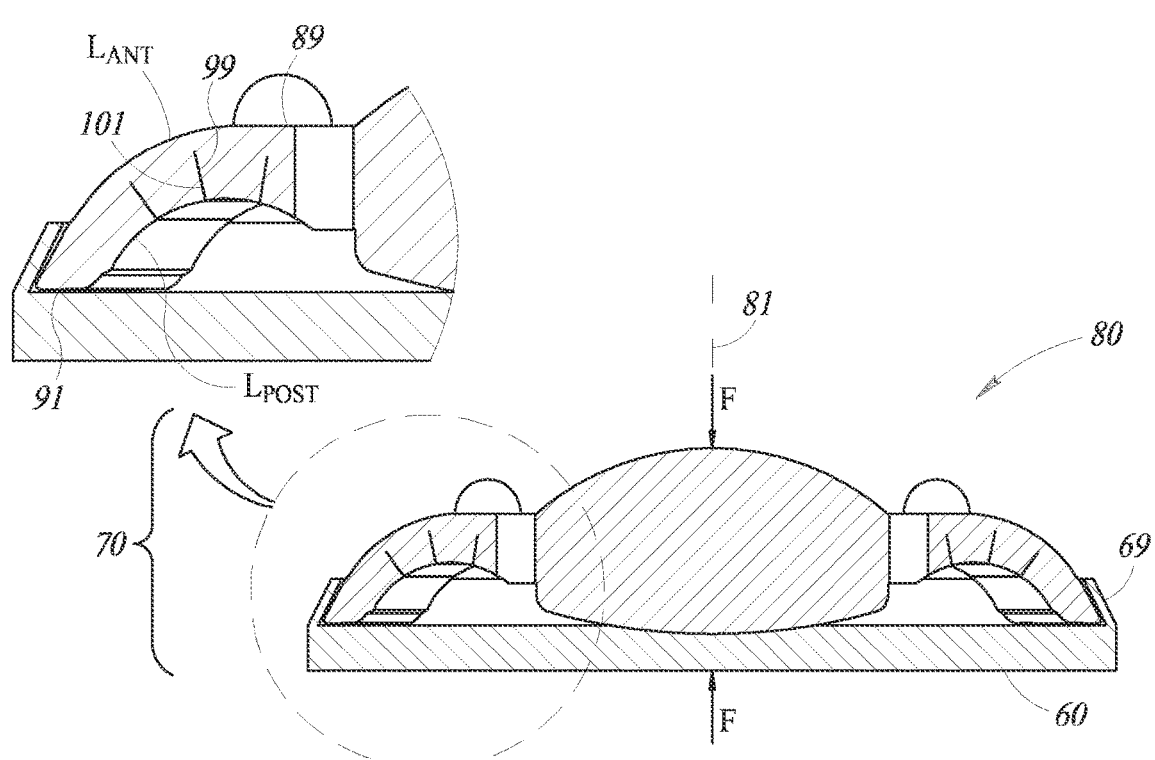
FIG. 13 is a transverse cross section of an assembled hybrid AIOL assemblage including the FIG. 9 discrete lens unit co-directional with the discrete lens unit axis along line 11-11 in FIG. 10 on application of a compression force F representative of a maximal accommodative physiological force for distance vision and an encircled section shown enlarged.

FIG. 12 and FIG. 13 show the discrete lens unit 80 in a contracted ciliary body state and a relaxed ciliary body state corresponding to near vision and distance vision. In FIG. 12, in the absence of an accommodative physiological force, the segmented lens haptics 88 are sufficiently stiff to separate the lens optics 82 from the discrete base member 60. The anterior lens haptics surface 92 has a length LANT between its lens haptics affixed end 89 and its lens haptics free end 91. The posterior lens haptics surface 93 has a length LPOST between its lens haptics affixed end 89 and its lens haptics free end 91. In the absence of an accommodative physiological force, each segmented lens haptics 88 has a staggered arcuate shape due to the presence of the grooves 97 between the inflexible lens haptics segments 103.

In FIG. 13, the segmented lens haptics 88 undergo elastic deformation on application of a compression force F representative of a maximal accommodative physiological force for distance vision as evidenced by flexing of the flexible lens haptics segments 102 and non-flexing of the inflexible lens haptics segments 103. Such compression force F effectively closes the grooves 97 between the inflexible lens haptics segments 103 such that the pairs of opposing surfaces 99 and 101 are in intimate contact. The anterior lens haptics surface 92 has a length LANT between its lens haptics affixed end 89 and its lens haptics free end 91 which is substantially the same as in FIG. 12. But the posterior lens haptics surface 93 has a length LPOST between its lens haptics affixed end 89 and its lens haptics free end 91 which is shorter than in FIG. 12. On application of a maximal accommodative physiological force, each segmented lens haptics 88 has a continuous non-staggered arcuate shape due to the absence of the grooves 97 between the inflexible lens haptics segments 103. On application of a maximal accommodative physiological force, each segmented lens haptics 88 becomes a rigid arched structure such that the discrete lens unit 80 as a whole becomes a rigid structure. In a return absence of the compression force F, the flexible lens haptics segments 102 react to restore the separation between the lens optics 82 and the discrete base member 60 in a lens haptics recovery time comparable to a human's natural response time thereby precluding undesirable unnatural visual phenomena, for example, a slower than natural focusing on an object.

Flexible lens haptics segments 102 can be designed such that some flexible lens haptics segments are more flexible to an accommodative physiological force than others. Such graded flexibility affords a controlled staggered compaction of a lens optics 82 towards a discrete base member 60 on application of an accommodative physiological force for distance vision. Conversely such graded flexibility affords a controlled staggered separation of a lens optics 82 from a discrete base member 60 on removal of an accommodative physiological force for near vision.

Figure 15:
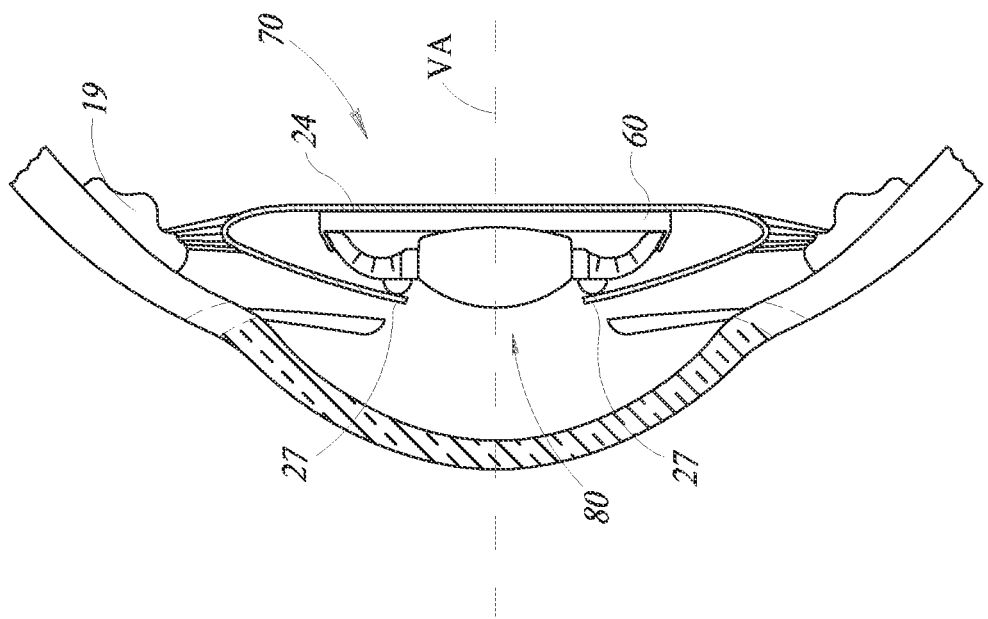
FIG. 15 is a cross section of an implanted hybrid AIOL assemblage including the FIG. 9 discrete lens unit for distance vision.
Figure 14:
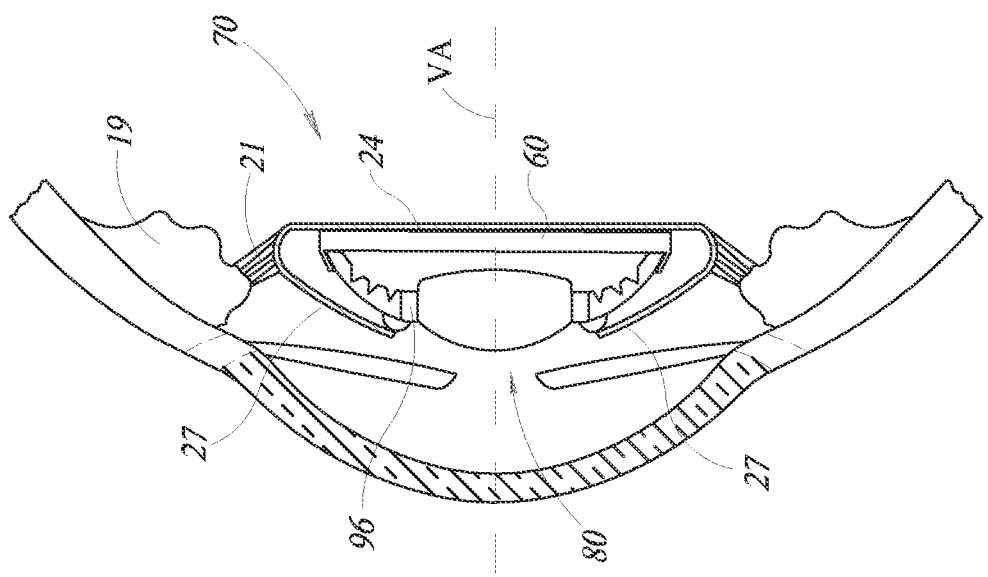
FIG. 14 is a cross section of an implanted hybrid AIOL assemblage including the FIG. 9 discrete lens unit for near vision.

FIG. 14 and FIG. 15 are transverse cross sections of an implanted hybrid AIOL assemblage 70 correspondingly for near vision and distance vision. The throughgoing haptics manipulation apertures 96 lie interior to the annular anterior capsular flange 27 therefore affording convenient access thereto for dialing the discrete lens unit 80 to its correct position in an implanted eye.

Figure 16:
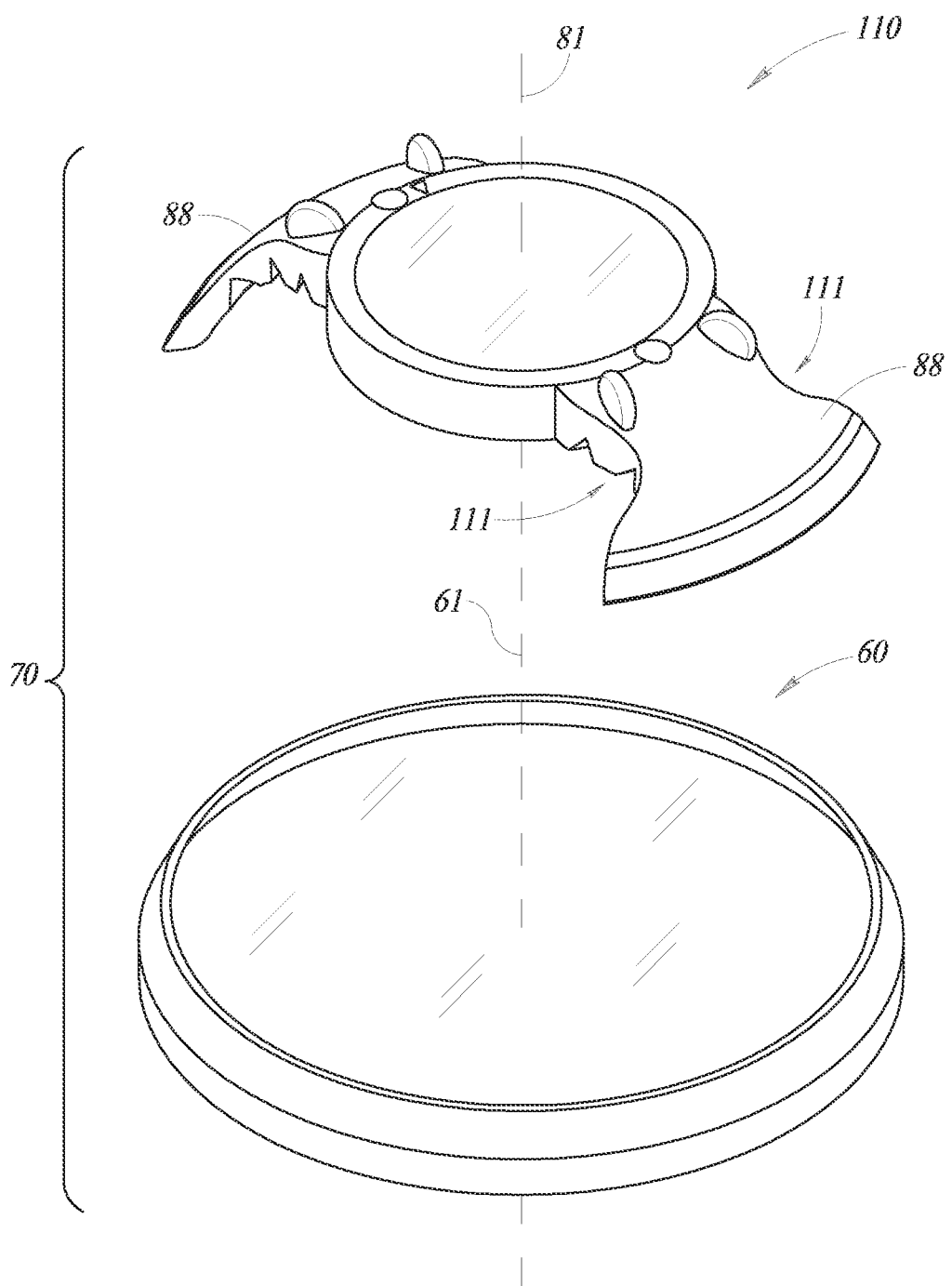
FIG. 16 is a front perspective view of an alternative modified WO 2017/203517 hybrid AIOL assemblage before assembly.
Figure 17:
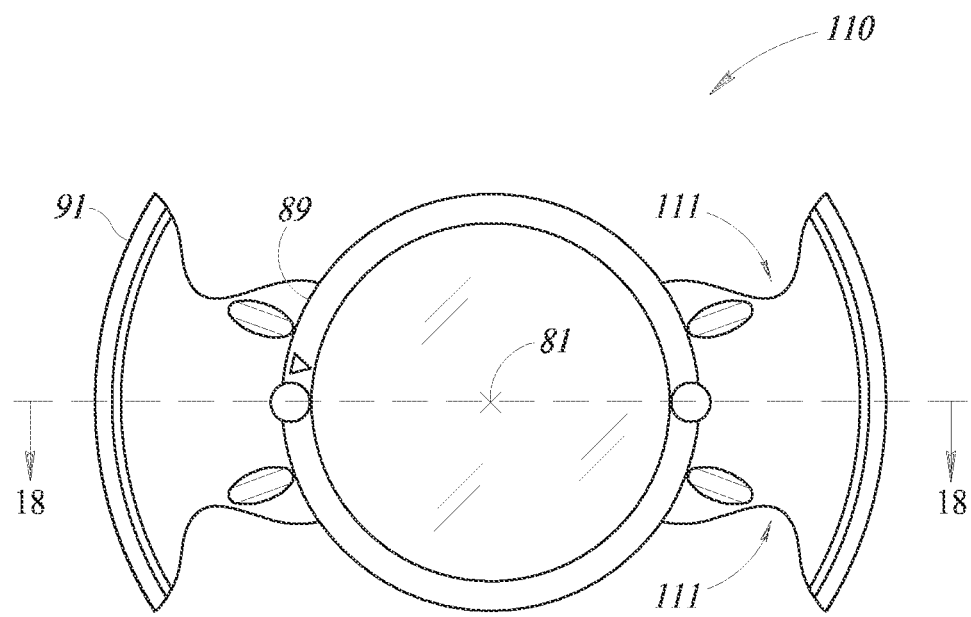
FIG. 17 is a top plan view of the FIG. 16 discrete lens unit.
Figure 18:
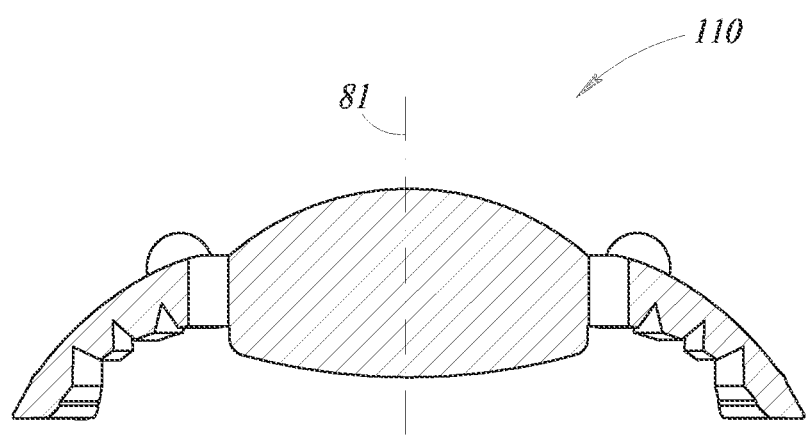
FIG. 18 is a transverse cross section of the FIG. 16 discrete lens unit co-directional with a discrete lens unit axis of the discrete lens unit along line 18-18 in FIG. 17.

FIG. 16 to FIG. 18 show a hybrid AIOL assemblage 70 including a discrete lens unit 110 similar to the discrete lens unit 80 and therefore similar parts are likewise numbered. The discrete lens unit 110 differs from the discrete lens unit 80 insofar as its segmented lens haptics 88 have an opposite pair of cutouts 111 between its lens haptics affixed end 89 and its lens haptics free end 91. Accordingly, the segmented lens haptics 88 has a smaller arc length between the pair of cutouts 111 compared to its arc length at its lens haptics affixed end 89 and its arc length at its lens haptics free end 91 in a top plan view of the discrete lens unit 110.

While the invention has been described with respect to a limited number of embodiments, it will be appreciated that many variations, modifications, and other applications of the invention can be made within the scope of the appended claims.

The invention claimed is:

1. A discrete lens unit for use with a discrete base member in a hybrid accommodating intraocular lens assemblage for implantation in a post-capsulorrhexis human eye having a visual axis, an annular ciliary body, and a vacated capsular bag having an annular anterior capsule flange and an intact posterior capsule, the ciliary body having a relaxed ciliary body state for distance vision and a contracted ciliary body state for near vision, the ciliary body peripherally tensioning the capsular bag on its relaxation from its contracted ciliary body state to its relaxed ciliary body state, the discrete base member having a base member axis and including a flat circular base member centerpiece and a peripheral base member surround, the flat circular base member centerpiece having a base member centerpiece refractive index, an anterior base member centerpiece surface and a posterior base member centerpiece surface, the discrete base member having an elevated circumferential retainer bounding a circumferential groove with the anterior base member centerpiece surface, the discrete lens unit having a discrete lens unit axis for co-axial alignment with the visual axis, the discrete lens unit comprising:

i) a lens optics having a lens optics refractive index, an anterior lens optics surface with a primary optical power for the distance vision and a posterior lens optics surface having a central circle with an additional optical power to said primary optical power for the near vision, and ii) at least two spaced apart shape memory resiliently flexible lens haptics radially extending from said lens optics for insertion in the circumferential groove for anchoring the discrete lens unit on the discrete base member for urging said lens optics away from the discrete base member for separating said posterior lens optics surface from the anterior base member centerpiece surface, each said shape memory resiliently flexible lens haptics having an anterior lens haptics surface and a posterior lens haptics surface correspondingly facing in the directions of said anterior lens optics surface and said posterior lens optics surface, and wherein the base member centerpiece and said lens optics have the same refractive index with each other, and whereupon, pursuant to an initial implantation of the discrete base member in the vacated capsular bag and a subsequent implantation of said discrete lens unit in the vacated capsular bag between the discrete base member and the anterior capsule flange, in the relaxed ciliary body state, the vacated capsular bag applies a maximal accommodative physiological force of the human eye on the discrete lens unit and the discrete base member such that said posterior lens optics surface is intimately immerged in the anterior base member centerpiece surface for creating a single refractive index optical continuum nullifying said posterior lens optics surface's additional optical power whereby the hybrid accommodating intraocular lens assemblage has said primary optical power for the distance vision only, and in the contracted ciliary body state, the vacated capsular bag enables said at least two spaced apart shape memory resiliently flexible lens haptics to space apart said lens optics from the discrete base member such that said posterior lens optics surface is spaced apart from the anterior base member centerpiece surface for adding said central circle's additional optical power to said anterior lens optics surface's primary optical power whereby the hybrid accommodating intraocular lens assemblage has a combined optical power for the near vision, wherein:

each said shape memory resiliently flexible lens haptics is constituted by a segmented lens haptics which includes a flexible lens haptics segment between said lens optics and an inflexible lens haptics segment within the range of the maximal accommodative physiological force of the human eye such that, on relaxation of the vacated capsular bag from its contracted ciliary body state to its relaxed ciliary body state, said segmented lens haptics flexes at said flexible lens haptics segment and does not flex at said inflexible lens haptics segment, each said segmented lens haptics having a generally circumferential groove in its posterior lens haptics surface for forming the flexible lens haptics segment whereby, in the contracted ciliary body state, each said posterior lens haptics surface appears as a staggered arcuate shape in a transverse cross section of the discrete lens unit co-directional with the discrete lens unit axis, and in the relaxed ciliary body state, said circumferential groove is closed such that each said posterior lens haptics surface appears as a continuous arcuate shape in the transverse cross section of the discrete lens unit co-directional with the discrete lens unit axis whereby each said segmented lens haptics becomes a rigid arched structure whereupon the discrete lens unit as a whole becomes a rigid structure.

2. The discrete lens unit according to claim 1 and further comprising a lens optics surround surrounding said lens optics wherein said at least two spaced apart shape memory resiliently flexible lens haptics radially extend from said lens optics surround.

3. The discrete lens unit according to claim 2 wherein each of said segmented lens haptics has an adjacent haptics manipulation aperture at least partially located in said lens optics surround.

4. The discrete lens unit according to claim 3 wherein each of said segmented lens haptics includes at least one pair of cutouts located opposite one another in respective lateral sides of said segmented lens haptics and extending on each lateral side of said segmented lens haptics between an affixed end and a free end of said segmented lens haptics whereby said segmented lens haptics has a smaller circumferential arc length between said pair of cutouts compared to an arc length at said affixed end and an arc length at said free end in a top plan view of said anterior lens optics surface.

5. The discrete lens unit according to claim 3 wherein each of said flexible lens haptics segment includes a first flexible lens haptics segment and a second flexible lens haptics segment spaced apart from said first flexible lens haptics segment where said first flexible lens haptics segment is more flexible than said second flexible lens haptics segment to the accommodative physiological force of the human eye.

6. The discrete lens unit according to claim 2 wherein each of said segmented lens haptics includes at least one pair of cutouts located opposite one another in respective lateral sides of said segmented lens haptics and extending on each lateral side of said segmented lens haptics between an affixed end and a free end of said segmented lens haptics whereby said segmented lens haptics has a smaller circumferential arc length between said pair of cutouts compared to an arc length at said affixed end and an arc length at said free end in a top plan view of said anterior lens optics surface.

7. The discrete lens unit according to claim 2 wherein each of said flexible lens haptics segment includes a first flexible lens haptics segment and a second flexible lens haptics segment spaced apart from said first flexible lens haptics segment where said first flexible lens haptics segment is more flexible than said second flexible lens haptics segment to the accommodative physiological force of the human eye.

8. The discrete lens unit according to claim 1 wherein each of said segmented lens haptics includes at least one pair of cutouts located opposite one another in respective lateral sides of said segmented lens haptics and extending on each lateral side of said segmented lens haptics between an affixed end and a free end of said segmented lens haptics whereby said segmented lens haptics has a smaller circumferential arc length between said pair of cutouts compared to an arc length at said affixed end and an arc length at said free end in a top plan view of said anterior lens optics surface.

9. The discrete lens unit according to claim 8 wherein each of said flexible lens haptics segment includes a first flexible lens haptics segment and a second flexible lens haptics segment spaced apart from said first flexible lens haptics segment where said first flexible lens haptics segment is more flexible than said second flexible lens haptics segment to the accommodative physiological force of the human eye.

10. The discrete lens unit according to claim 1 wherein each of said flexible lens haptics segment includes a first flexible lens haptics segment and a second flexible lens haptics segment spaced apart from said first flexible lens haptics segment where said first flexible lens haptics segment is more flexible than said second flexible lens haptics segment to the accommodative physiological force of the human eye.

* * * * *